US00PP09268P

United States Patent [19]

Jessel, Jr.

[11] Patent Number: Plant 9,268

[45] Date of Patent: Aug. 29, 1995

[54] CARNATION PLANT NAMED 'CFPC DART'

[75] Inventor: Walter H. Jessel, Jr., Salinas, Calif.

[73] Assignee: California Florida Plant Co., L.P., Salinas, Calif.

[21] Appl. No.: 315,133

[22] Filed: Sep. 29, 1994

[51] Int. Cl.[6] ..... A01H 5/00

[52] U.S. Cl. ..... Plt./70.7

[58] Field of Search ..... Plt. 70.7

*Primary Examiner*—James R. Feyrer

*Attorney, Agent, or Firm*—Christie, Parker & Hale

[57] ABSTRACT

A new dwarf carnation plant suitable for growing in pots producing crimson red flowers.

1 Drawing Sheet

SUMMARY OF THE INVENTION

The present invention relates to a new and distinct dwarf variety of carnation plant which was originated by me in a controlled breeding program by my crossing as seed and pollen parents, two proprietary, unnamed and unpatented seedlings of my creation. The varietal denomination of this new carnation is 'CFPC Dart'.

Among the novel combination of characteristics possessed by the new variety which distinguishes it are dwarf growth habit not requiring application of growth retardants tolerance to temperatures as high as 120° F. and as low as 10° F. and ability to produce flower buds that will open in a home environment with moderate light conditions. Flowers of the new variety are of an attractive crimson red coloration.

Asexual reproduction by propagation by side shoot cuttings of the new variety as performed in Salinas, Calif., shows that the foregoing and other distinguishing characteristics come true to form and are established and transmitted through succeeding propagations.

Unlike preceding pot carnations, i.e., Lillipots (Sakata), Rocky Mountain Series (Goldsbury C.S.U.), and Knight Series (Goldsmith Seed Co.), CFPC pot carnations were selected and bred from indoor cut-types and are best grown under cover. The Lillipots etc. were bred from outdoor garden-types and species and are best grown outdoors. The CFPC pot varieties are dwarf due to a homozygous recessive dwarfing gene. If crossed to the aforementioned "pot-types", the resultant progeny returns to tall cut seedlings.

The Lillipots and Knight Series are seed crops. The Rocky Mountain and European pot varieties (cuttings) are no longer commercially available.

BRIEF DESCRIPTION OF ILLUSTRATION

The accompanying illustration shows typical specimens of the vegetative growth and flowers of the new variety depicted in color as nearly true as it is reasonably possible to make the same in a color illustration of this character. Although propagation by side shoot cuttings is described, other known methods of asexual reproduction may also be used to reproduce 'CFPC Dart'.

DESCRIPTION OF THE NEW VARIETY

The following is a detailed description of my new variety, with color terminology in accordance with the Royal Horticultural Society Color Chart (RHSCC). The terminology used in color description herein refers to plate numbers in the aforementioned color chart.

Color designations and color descriptions may deviate from the stated values depending upon varying environmental, seasonal and cultural conditions.

The information provided herein is based on observations of plants grown inside commercial greenhouses at Salinas, Calif. The height of plant and flower and foliage size are established as an average using standard commercial cultural practices.

Name: CFPC Dart.

Classification:

*Botanical.*—*Dianthus caryophyllus.*

*Commercial.*—Carnation, dwarf, pot type.

Parentage:

*Female parent.*—Unnamed seedling (No. 890404).

*Male parent.*—Unnamed seedling (No. 890421).

Plant:

*Height.*—About 6 inches.

*Growing habit.*—Herbaceous, semi-upright, pot type.

*Blooming habit.*—As a spray.

*Blooming season.*—Year round.

*Rooting time.*—About 13 days.

*Mutation prone.*—No.

*Disease resistance.*—Unknown at present.

*Temperature tolerance.*—120° F. to 10° F.

*Breaking action.*—Good, average about 7.

Foliage:

*Color.*—Upper side: Near 131B. Lower side: Near 131C.

*Size.*—About 3½-inches.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Green.

Bud:

*Shape.*—Oval.

*Color.*—Green.

*Length.*—About ⅓-inch.

*Diameter.*—About 1/5-inch.

Calyx:

*Number of sepals.*—About 6.

*Length.*—About ⅓-inch.

*Width.*—About 1/5-inch.

*Color.*—Outside — near 141C. Inside — near 142C.

Bloom:

*Shape.*—Round.

*Size.*—Diameter average: About 1⅛-inches. Depth average: About ¾-inch.

*Borne.*—As a spray.

*Color.*—General tonality: Crimson red. Upper side: Near 46A. Lower side: Near to from 53C to 53D. Center: Near to from 53A to 53B. Outer petals: Near 53A.

*Keeping quality.*—3 to 4 weeks on plant.

*Fragrance.*—Slight.

Petals:

*Number.*—About 39.

*Outer petals.*—Length: About 1-inch. Width: About 1-inch.

*Central petals.*—Length: About ½-inch. Width: About ⅓-inch.

*Texture.*—Smooth.

*Form.*—Fan shaped.

*Appearance.*—Shiny.

Reproductive organs:

*Stamens.*—Number: About 14. Arrangement: Around the ovary.

*Anthers.*—Length: About 1/10-inch. Color: Near 77A.

*Filaments.*—Length: About 1-inch. Color: Near to 157C.

*Pistil.*—Number: About 2. Color: Near 155B. Length: About 1/5-inch.

*Stigma.*—Number: About 2. Color: Near 71B.

*Ovary.*—Shape: Conical. Color: Base — tannish green. Body — green.

*Fertility.*—Female — good. Male — excellent.

I claim:

1. A new and distinct dwarf variety of carnation plant named 'CFPC Dart', substantially as shown and described.

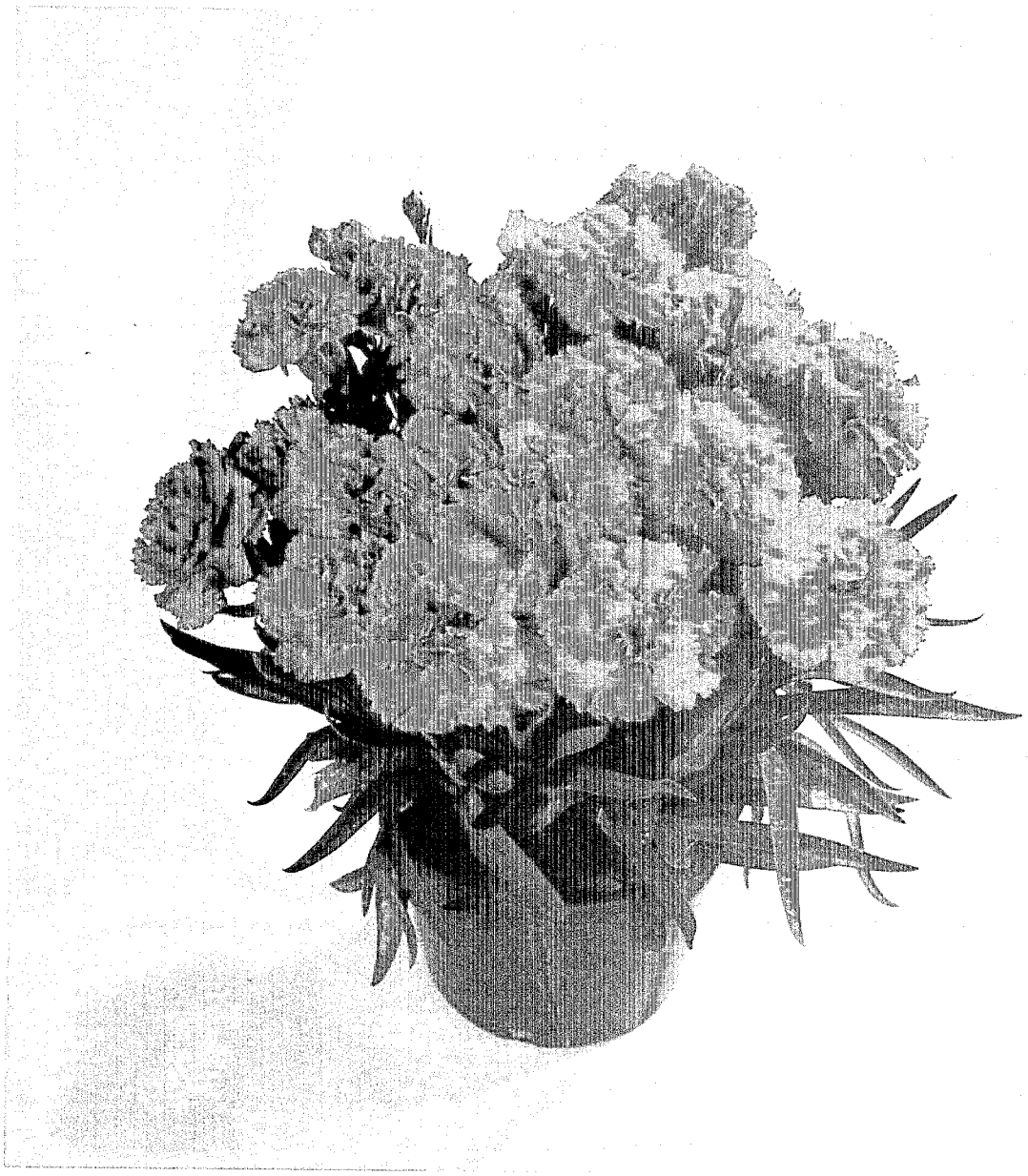

* * * * *